(12) United States Patent
Sheldon et al.

(10) Patent No.: US 11,766,572 B2
(45) Date of Patent: *Sep. 26, 2023

(54) IMPLANTABLE MEDICAL DEVICE WITH LOCKING DATUM ARRANGEMENT BETWEEN DF4/IS4 ASSEMBLY AND HEADER

(71) Applicant: Pacesetter, Inc., Sylmar, CA (US)

(72) Inventors: Evan Sheldon, Sherman Oaks, CA (US); Armando M. Cappa, Granada Hills, CA (US); Christopher J. Fleck, Santa Clarita, CA (US); Arees Garabed, North Hills, CA (US)

(73) Assignee: Pacesetter, Inc., Sylmar, CA (US)

( * ) Notice: Subject to any disclaimer, the term of this patent is extended or adjusted under 35 U.S.C. 154(b) by 528 days.

This patent is subject to a terminal disclaimer.

(21) Appl. No.: 16/898,656

(22) Filed: Jun. 11, 2020

(65) Prior Publication Data

US 2020/0298010 A1    Sep. 24, 2020

Related U.S. Application Data

(62) Division of application No. 15/796,054, filed on Oct. 27, 2017, now Pat. No. 10,716,947.

(60) Provisional application No. 62/436,896, filed on Dec. 20, 2016.

(51) Int. Cl.
*A61N 1/375* (2006.01)
*A61N 1/378* (2006.01)
*A61N 1/36* (2006.01)
*H01R 13/639* (2006.01)
*H01R 13/52* (2006.01)
*A61N 1/372* (2006.01)
*A61N 1/05* (2006.01)

(52) U.S. Cl.
CPC ......... *A61N 1/3754* (2013.01); *A61N 1/3606* (2013.01); *A61N 1/3752* (2013.01); *A61N 1/3787* (2013.01); *H01R 13/5224* (2013.01); *H01R 13/639* (2013.01); *A61N 1/05* (2013.01); *A61N 1/37211* (2013.01); *A61N 1/37247* (2013.01); *A61N 1/37512* (2017.08)

(58) Field of Classification Search
CPC ... A61N 1/3754; A61N 1/3752; A61N 1/3787
See application file for complete search history.

(56) References Cited

U.S. PATENT DOCUMENTS 6,741,892 B1 * 5/2004 Meadows ............ A61N 1/3752
607/116
2013/0065443 A1 * 3/2013 Jullien .................. H01R 43/24
439/620.03

* cited by examiner

*Primary Examiner* — Joseph M Dietrich
(74) *Attorney, Agent, or Firm* — THE SMALL PATENT LAW GROUP LLC; Dean D. Small (57) ABSTRACT

Disclosed herein is an implantable electronic device. The device includes a housing and a header connector assembly coupled to the housing. The header connector assembly includes a DF4/IS4 assembly and a header including a bore. The DF4/IS4 assembly is locked within the bore via a locking datum arrangement that exists between the DF4/IS4 assembly and the header.

20 Claims, 8 Drawing Sheets

IMPLANTABLE MEDICAL DEVICE WITH LOCKING DATUM ARRANGEMENT BETWEEN DF4/IS4 ASSEMBLY AND HEADER

CROSS REFERENCE TO RELATED APPLICATIONS

The present application is a divisional application of U.S. application Ser. No. 15/796,054 filed Oct. 27, 2017, which application claims priority to U.S. provisional application No. 62/436,896 filed Dec. 20, 2016. The contents of the above-mentioned patent applications are hereby incorporated by reference in their entirety.

FIELD OF THE INVENTION

Aspects of the present invention relate to medical apparatus and methods. More specifically, the present invention relates to pulse generators and systems and methods for assembling pulse generators.

BACKGROUND OF THE INVENTION

Implantable pulse generators (IPGs) such as pacemakers and implantable cardioverter defibrillators (ICDs), which are used in the treatment of cardiac conditions, and neuromodulators or neurostimulators, which are used in chronic pain management or the actuation and control of other body systems, commonly include a housing, feedthrus, and a connector assembly that is enclosed in a header. Electrical stimulation originating in the housing is led to the connector assembly through feedthrus. The connector assembly serves to transmit electrical signals out of the IPG and to a lead electrically connected to the connector assembly, the lead transmitting electrical signals between the IPG and patient tissue.

Current header casting manufacturing processes and the associated methods of assembling the header and its enclosed connector assembly onto the housing require multiple operations, are skill intensive, and unavoidably time consuming. For example, at least some current cast-on header designs with quad pole (DF4/IS4) connectors require DF4/IS4 components to be stacked onto an inner core in in an arbor press to form a DF4/IS4 assembly. Once the tip block is placed on the end of the inner core, the entire stack of components is compressed axially together along the inner core using the arbor press. With the stack of components so compressed, a set screw of the tip block is tightened down on the inner core to lock the stack of components in the compressed state, thereby forming the DF4/IS4 assembly. The DF4/IS4 assembly is then placed into a mold for casting headers and, once molded, the cast header is attached to the housing (e.g., can) of the pulse generator via additional skill intensive and time consuming processes.

Injection molded headers are considered to be a way of reducing manufacturing costs. In at least some versions of the injection molding of headers, the DF4/IS4 tip block must be overmolded into the header. Unfortunately, some of the DF4/IS4 components are not capable of withstanding the high pressures of injection molding (e.g., upwards of 20,000 psi), resulting in the components needing to be installed after the injection molded header is procured. Without the DF4/IS4 tip block, the stack of components can no longer be locked as a sub-assembly prior to installation into the header, thereby increasing manufacturing complexity, costs and time.

There is a need in the art for systems and methods that reduces the complexity, time, and costs associated with the manufacturing headers employing DF4/IS4 connectors.

BRIEF SUMMARY OF THE INVENTION

Disclosed herein is an implantable electronic device. In one embodiment, the device includes a housing and a header connector assembly coupled to the housing. The header connector assembly includes a DF4/IS4 assembly and a header including a bore. The DF4/IS4 assembly is locked within the bore via a locking datum arrangement that exists between the DF4/IS4 assembly and the header.

In one embodiment, the locking datum arrangement is a push and twist locking datum arrangement. Thus, the DF4/IS4 assembly is pushed into the bore and then twisted within the bore to lock the DF4/IS4 arrangement within the bore via the locking datum arrangement.

In one embodiment, the DF4/IS4 assembly includes a strain relief and the locking datum arrangement exists between the strain relief and the header.

In one embodiment, the locking datum arrangement includes a male portion on the DF4/IS4 assembly and a female portion on the header. The male portion is received in the female portion when the DF4/IS4 assembly is locked within the bore via the locking datum arrangement.

In one embodiment, the locking datum arrangement includes a female portion on the DF4/IS4 assembly and a male portion on the header. The male portion is received in the female portion when the DF4/IS4 assembly is locked within the bore via the locking datum arrangement.

In one embodiment, the locking datum arrangement includes a key and a datum notch. The key radially extends from the DF4/IS4 assembly and the datum notch radially extends from the bore into the header. The key is received in the datum notch when the DF4/IS4 assembly is locked within the bore via the locking datum arrangement.

The bore may include a groove that extends proximally from a distal opening of the bore, the groove being sized and shaped to receive the key as the DF4/IS4 is inserted into the bore. The datum notch may extend from the groove such that the DF4/IS4 assembly can be rotated to cause the key to exit the groove and enter the datum notch. A distal face of the key may make abutting contact with a distal datum wall of the datum notch when the DF4/IS4 assembly is locked within the bore via the locking datum arrangement.

In one embodiment, the device further includes an implantable lead including a DF4/IS4 connector end receivable within a receptacle defined by at least a portion of the DF4/IS4 assembly. The device may be an implantable pulse generator.

Also disclosed herein is a method of manufacturing an implantable electronic device. In one embodiment the method includes: inserting a DF4/IS4 assembly into a bore of a header; and rotating the DF4/IS4 assembly within the bore to engage a locking datum arrangement that exists between the DF4/IS4 assembly and the header, the locking datum arrangement preventing the DF4/IS4 assembly from being withdrawn from the bore.

In one embodiment, the DF4/IS4 assembly is supported on a core pin when the DF4/IS4 assembly is inserted into the bore.

In one embodiment, the header includes a tip block embedded in the header. A free end of the core pin projects proximally from the DF4/IS4 assembly. The free end is received in the tip block before the DF4/IS4 assembly is rotated to engage the locking datum arrangement.

In one embodiment, the bore includes a groove that extends proximally from a distal opening of the bore. The DF4/IS4 assembly includes a key radially extending from the DF4/IS4 assembly. The key moves along the groove when the DF4/IS4 assembly is inserted into the bore.

In one embodiment, a datum notch extends from the bore into the header. Rotating the DF4/IS4 assembly causes the key to extend into the datum notch, thereby engaging the locking datum arrangement.

In one embodiment, engaging the locking datum arrangement compresses the DF4/IS4 assembly.

In one embodiment, the DF4/IS4 assembly and header, when locked together via the locking datum arrangement, form at least part of a header connector assembly. In such a situation, the method may further include welding the header connector assembly to a housing of the implantable electronic device. The method may continue with epoxy backfilling of the header connector assembly.

Depending on the embodiment, the method may result in an implantable electronic device that is an implantable pulse generator.

While multiple embodiments are disclosed, still other embodiments of the present disclosure will become apparent to those skilled in the art from the following detailed description, which shows and describes illustrative embodiments of the disclosure. As will be realized, the invention is capable of modifications in various aspects, all without departing from the spirit and scope of the present disclosure. Accordingly, the drawings and detailed description are to be regarded as illustrative in nature and not restrictive.

DETAILED DESCRIPTION

Implementations of the present disclosure involve an implantable electronic device such as an implantable cardiac device (ICD) or an implantable pulse generator (IPG). The IPG administers electrotherapy or other neurostimulation via an implantable lead having a lead connector end on a proximal end of the implantable lead. The IPG includes a housing or can and a connector assembly enclosed in a header to form a header connector assembly that is coupled to the housing or can. The header connector assembly has at least one DF4/IS4 assembly that defines at least one lead connector receiving bore or receptacle. The DF4/IS4 assembly includes electrical contacts of the connector assembly that make electrical contact with corresponding electrical terminals on the lead connector end on the proximal end of the implantable lead when the lead connector end is plugged into or otherwise received in the lead connector receiving bore or receptacle.

Via the electrical connection between the corresponding electrical terminals of the lead connector end and the electrical contacts of the lead connector receiving bore, electrical signals can be administered from the IPG and through the lead to patient tissue. Similarly, but in reverse, electrical signals originating in patient tissue can travel via the lead to the IPG to be sensed at the IPG.

The implantable electronic device configurations and methods of assembly disclosed herein are advantageous for at least the reason that they simplify the process of manufacturing the header connector assembly of an IPG, wherein the connector assembly employs DF4/IS4 assemblies. Specifically, a twist and lock interface between a strain relief of the DF4/IS4 assembly and a bore of an injection molded header is provided in the form of a keyed locking datum arrangement, which allows the DF4/IS4 assembly to be aligned, inserted, rotated, compressed, and locked together within the bore without the use of additional tooling. The keyed locking datum arrangement provides the axial compression required within the DF4/IS4 assembly to prevent epoxy from leaking into the components and spaces of the DF4/IS4 assembly when the DF4/IS4 assembly is being encapsulated in epoxy during the backfill process, and this benefit is provided without the use of any additional tooling or set screws. Additionally, there is no risk of damaging the pre-molded headers in tooling, no set screw is required to lock, and the keyed locking datum arrangement removes the variability in axial compression caused by manufacturing via an arbor press.

Before beginning a detailed discussion of the assembly of the header and the connector assembly employing DF4/IS4 assemblies to form the header connector assembly, a general discussion is first given regarding features of a DF4/IS4 lead connector end at the proximal end of an implantable medical lead followed by a general discussion of the features of an IPG.

A. Overview of a DF4/IF4 Connector End and an IPG.

Figure 1:
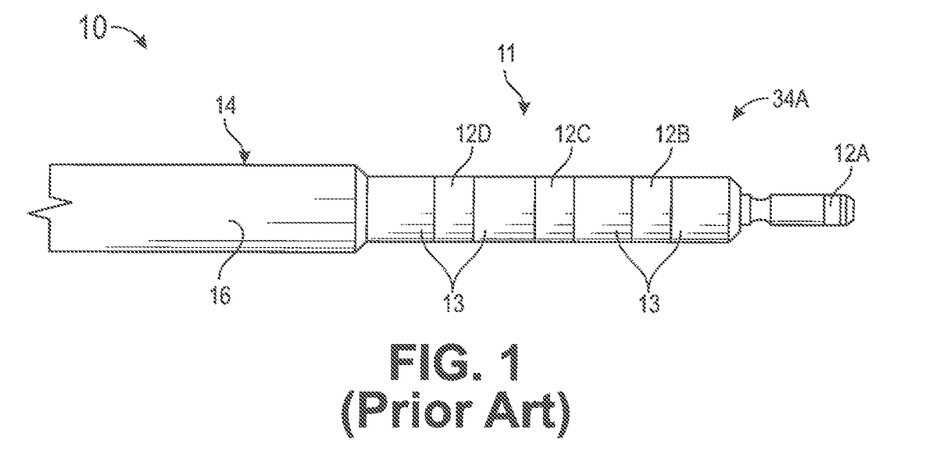
FIG. 1 is an isometric view of a proximal end portion (i.e., lead connector end) of a DF4/IS4 lead.

FIG. 1 shows a proximal end portion 10 of a conventional DF4/IS4 lead, but is generally representative of any type of implantable lead whether in the cardiac, pain management or other medical treatment space. The diameter of such a lead may be made a sufficiently small diameter to facilitate the lead's implantation into small veins such as those found in the coronary sinus region of the heart and to allow implantation of a plurality of leads into a single vessel for multi-site or multi-chamber pacing.

As is well known in the art, DF4/IS4 leads typically consists of a tubular housing of a biocompatible, biostable insulating material containing an inner multifilar conductor coil that is surrounded by an inner insulating tube. The inner conductor coil is connected to a tip electrode on the distal end of the lead.

In one embodiment and moving radially outwardly from the inner insulating tube is a series of surrounding concentric alternating layers of multifilar conductor coils and insulating tubes. Specifically, there may be two intermediate multifilar conductor coils and an outer multifilar conductor coil, each of the concentric coils being isolated from the other via an intervening concentric insulating tube. The entirety of these concentric coil layers and intervening concentric insulating tubes are enclosed within the outer tubular housing.

The two intermediate conductor coils and the outer conductor coil are individually connected to respective anodal ring electrodes and, in some cases, a defibrillation coil, all of which are located near the distal region of the lead. The layers of inner insulation tubes are intended to electrically isolate the conductor coils from each other, thereby preventing any internal electrical short circuit, while the housing protects the entire lead from the intrusion of body fluids. These insulating materials are typically either silicone rubber, polyurethane or a combination thereof.

In some embodiments, any one or more of the conductor coils may be replaced with a corresponding multifilar cable conductor. Such cable conductors may extend through respective wall lumens within a multilumen housing in order to reduce even further the overall diameter of the lead.

The proximal lead end portion 10 shown in FIG. 1 includes a lead connector end 11 that conforms to the DF4/IS4 standard and includes a plurality of proximal terminals or contacts, namely, a straight pin tip contact 12A, and three ring contacts 123, 12C, 12D, respectfully, as one advances in a distal direction. The pin tip contact 12A is electrically coupled to the tip electrode on the distal end of the lead via the inner conductor coil, and the ring contacts 12B, 12C, and 12D are electrically coupled to ring electrodes (and where applicable, a defibrillation coil) via the respective other intermediate and outer conductor coils or, alternatively, via conductor cables residing within lumens of the housing, Each of the plurality of contacts 12A, 12B, 12C. 12D is separated from its neighbor by a sealing surface 13. The lead connector end 11 proximally extends from the proximal end of the tubular lead body 14, which is enclosed by the above-described outer tubular housing 16.

The tip and ring terminals or contacts of the lead connector end may each be engaged by a conductive garter spring contact or other resilient electrical contact element in a corresponding lead connector receiving bore of the DF4/IS4 assembly of the connector assembly of the header connector assembly, the resilient electrical contact element being carried by a DF4/IS4 assembly of the connector assembly enclosed in the header as described below. The sealing surfaces 13 on the lead connector end 11 interface with spaced-apart pairs of seal rings in the lead connector receiving bore of the header connector assembly, the seal rings abutting against in a fluid-sealing manner the outer circumferential surface of the sealing surfaces 13 of the lead connector end 11, thereby preventing body fluids from reaching the electrical terminals and contacts when the lead connector end 11 is plugged into the corresponding lead connector receiving bore.

With the lead connector end 11 of the lead inserted in the lead connector receiving bore of the header connector assembly, the tip and ring terminals 12A, 12B, 12C, 12D are electrically coupled via the contacts of the DF4/IS4 assembly of the connector assembly and a feedthru to the electronic circuits within the hermetically sealed housing of the IPG (e.g., cardiac pacemaker, ICD, or other implantable tissue stimulation and/or sensing device such as those used in pain management, etc.).

Figure 2:
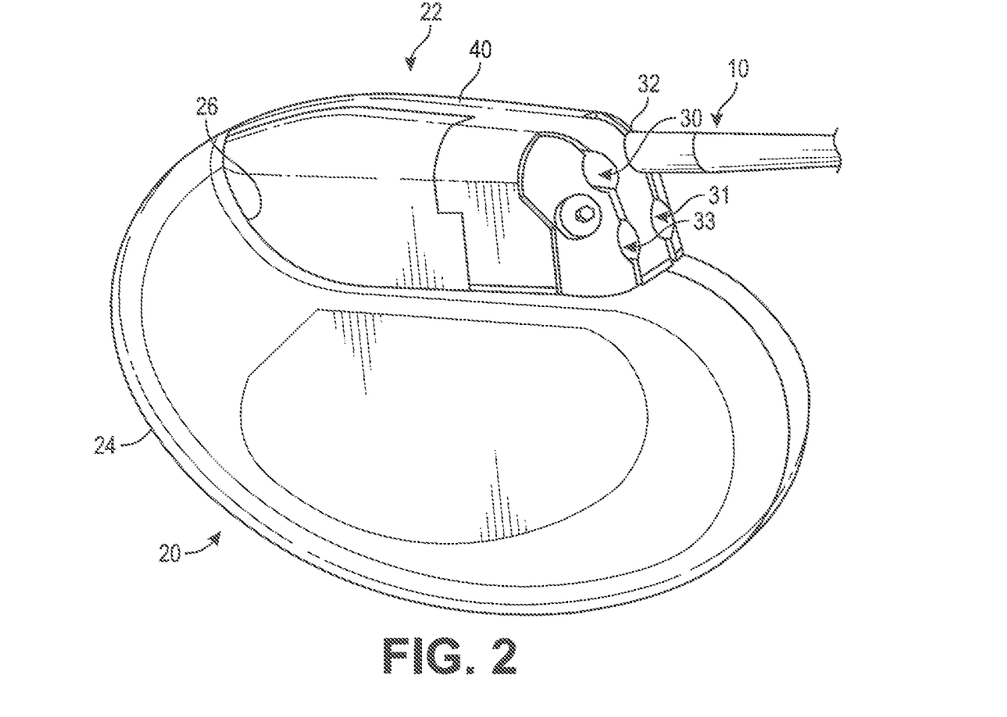
FIG. 2 is an isometric view of a cardiac pacemaker/defibrillator unit (i.e., implantable pulse generator (IPG)) incorporating connector junctions or terminals for communication with one or more electrodes.

FIG. 2 shows a multi-site or multi-chamber cardiac pacemaker/defibrillator unit that is generally representative of any type of IPG 20 incorporating a header connector assembly 22 coupled to a housing 24. The header connector assembly 22 includes a header 40 enclosing a connector assembly 42, both of which are depicted in the process of being assembled together in FIG. 4 discussed below. The IPG 20 is of a conventional design, including a hermetically sealed housing 24, which is also known as a can or casing. The housing 24 encloses the electronic components of the IPG 20 with the header connector assembly 22 mounted along a top surface 26 of the housing 24.

FIG. 2 illustrates that, in some embodiments, the header connector assembly 22 may include four or more lead connector receiving bores or receptacles 30, 31, 32, 33 for receiving the lead connector ends of four implantable leads. FIG. 2 also shows the proximal end portion 10 of a lead, wherein the lead connector end on the proximal end portion 10 of the lead is received in a corresponding receptacle 32. In other embodiments, the header connector assembly 22 includes two receptacles comprising a single pair of receptacles (i.e., receptacles 30 and 33) for receiving the proximal ends of leads such as, for example, conventional bipolar leads and/or conventional cardioverting and/or defibrillating leads.

Figure 3:
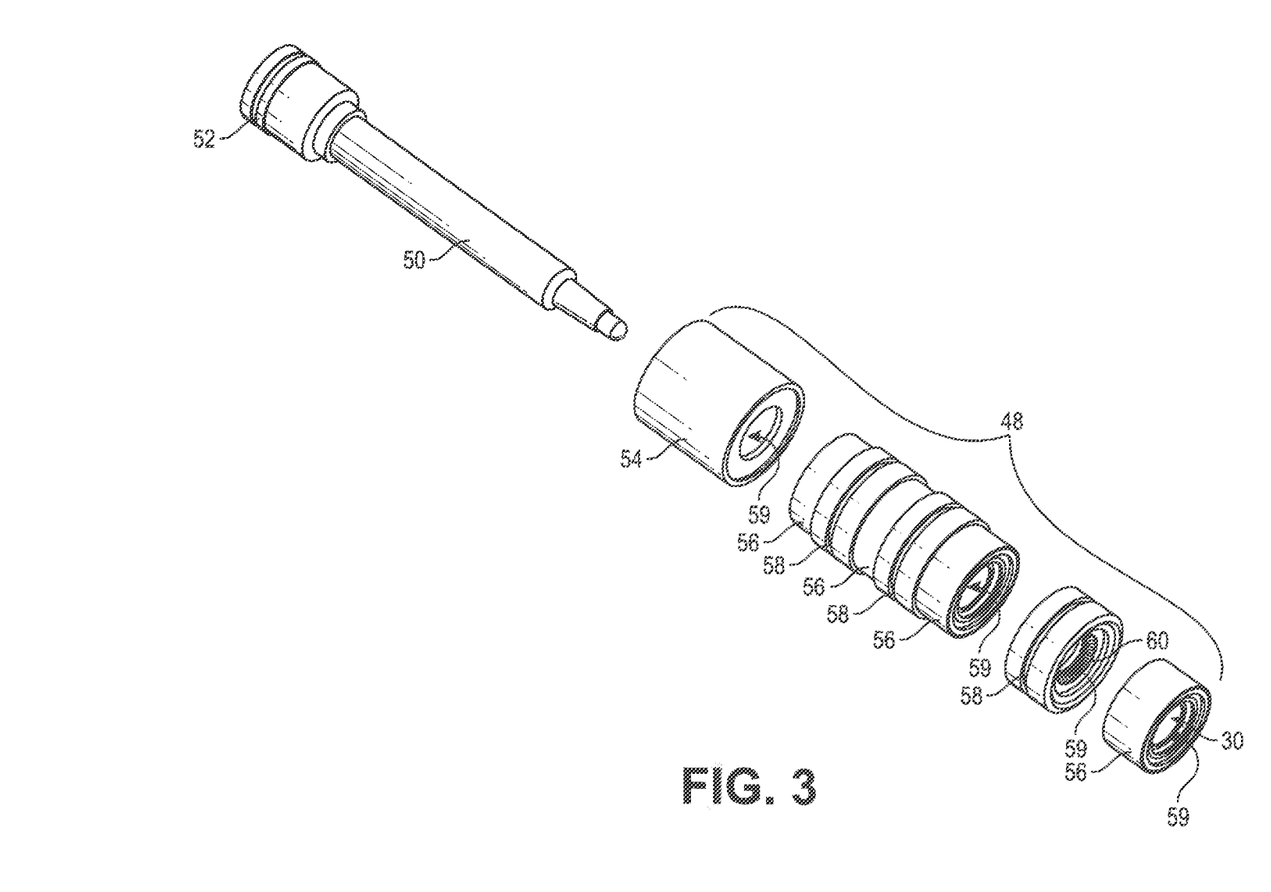
FIG. 3 is an exploded isometric view of a DF4/IS4 assembly and a core pin on which the DF4/IS4 assembly is assembled.

FIG. 3 is an exploded isometric view of a DF4/IS4 assembly 48 and a core pin 50 on which the DF4/IS4 assembly 48 is assembled. As shown in FIG. 3, the core pin 50 includes an O-ring 52 on a distal end of the core pin, and the DF4/IS4 assembly 48 includes a strain relief 54, four seal assemblies 56, and three contact assemblies 58. The strain relief, seal assemblies and contact assemblies are annular or donut-shaped and each have a central opening 59. When the strain relief, seal assemblies and contact assemblies are stacked together to form a DF4/IS4 assembly 48, the openings 59 combine to form a lead connector receiving bore or receptacle 30 of the header 40 of the header connector assembly 22.

As illustrated in FIG. 3, the central opening 59 of each contact assembly 58 of the DF4/IS4 assembly 48 contains a conductive garter spring contact 60 that biases into contact with the respective ring terminal 12B, 12C, 12D of the lead connector end 11 when the lead connector end is received in a lead connector receiving bore or receptacle 30 of the DF4/IS4 assembly 48.

B. Assembly of Header Connector Assembly onto IPG Housing.

Figure 4:
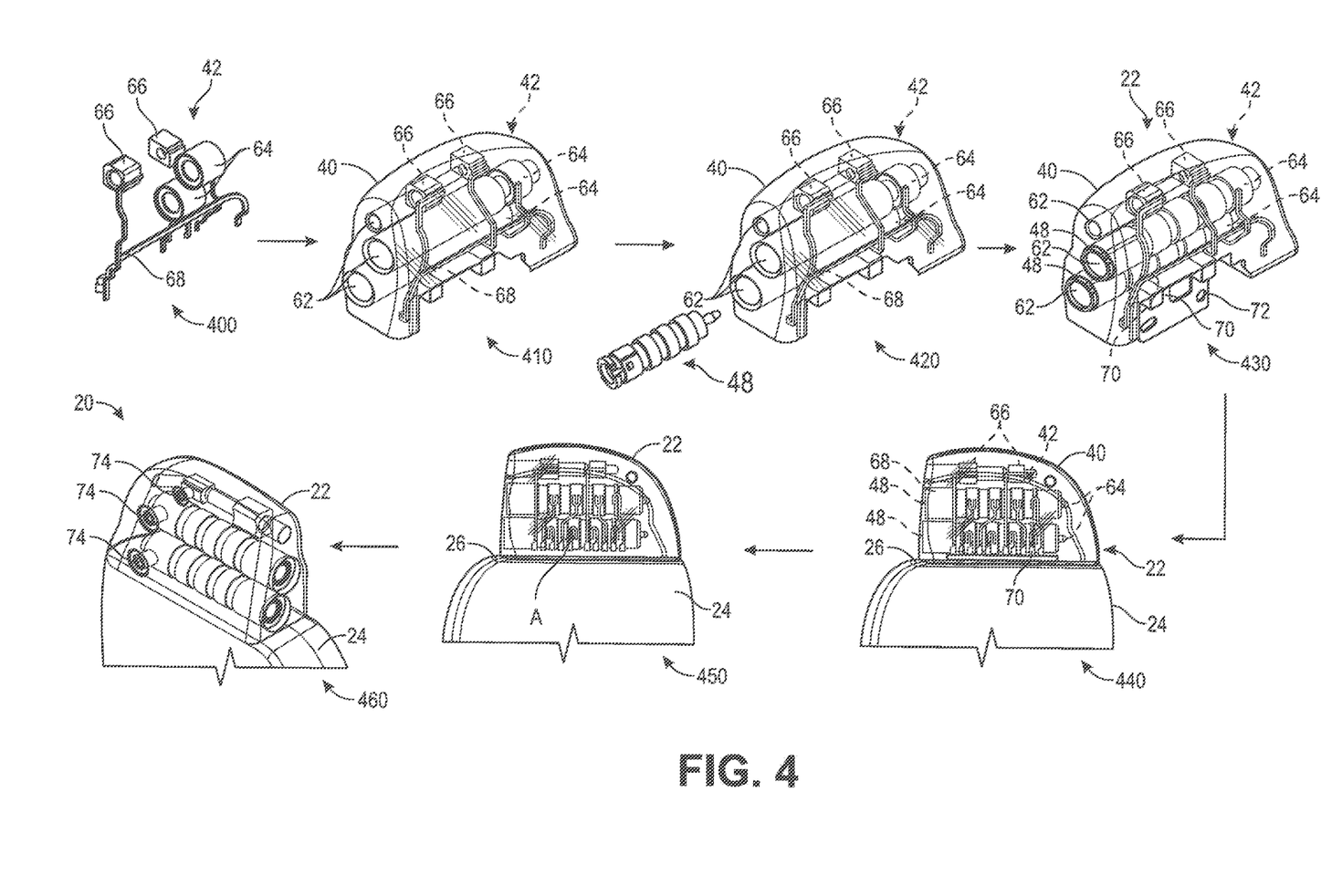
FIG. 4 is a series of isometric views illustrating the assembly of the header connector assembly from a header and a connector assembly that includes DF4/IS4 assemblies.
Figure 5:
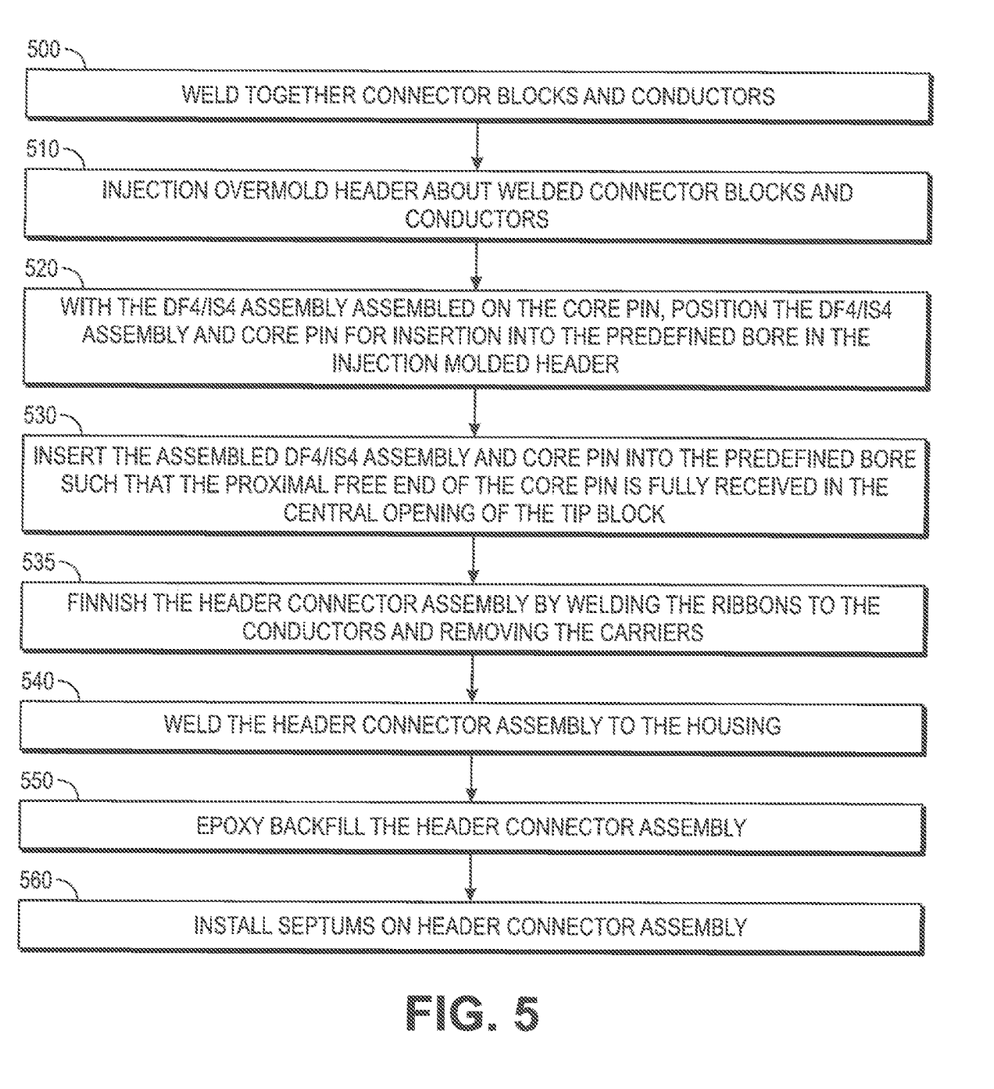
FIG. 5 is a flow chart outlining the process illustrated in FIG. 4.

FIG. 4 is a series of isometric views illustrating the assembly of the header connector assembly 22, and FIG. 5 is a flow chart outlining the process illustrated in FIG. 4. As can be understood from FIGS. 4 and 5, DF4/IS4 tip blocks 64, other connector blocks 66, and conductors 68 are welded together as indicated at 400 in FIG. 4 [block 500]. As shown at 410, these components 64, 66, 68 are overmolded by a header 40 via an injection molding process [block 510], the header including predefined bores 62 leading to, and coaxial with, the open centers of the blocks 64, 66.

Figure 6:
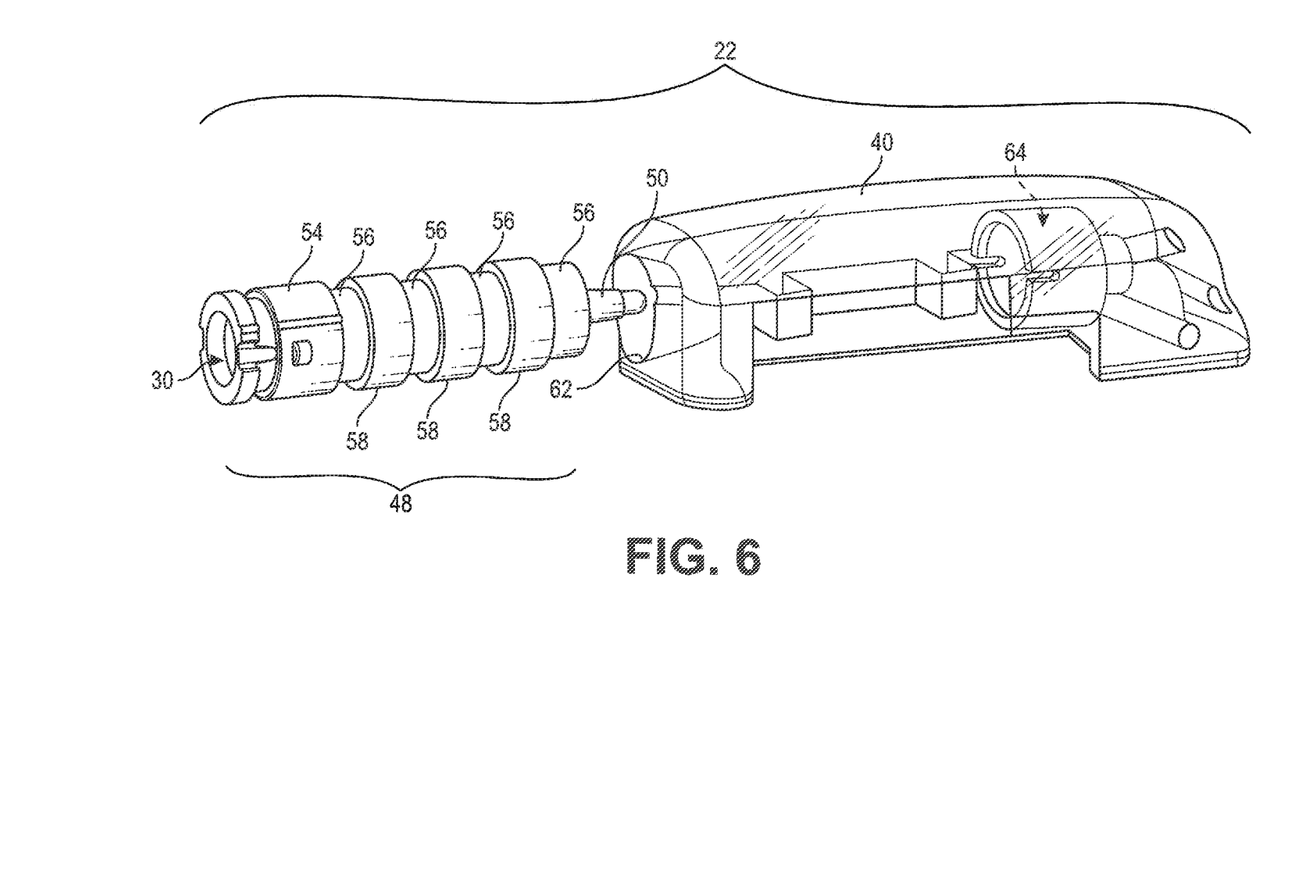
FIG. 6 is an isometric view of a step in the process outlined in FIGS. 4 and 5, wherein the DF4/IS4 assembly is assembled on the core pin, the core pin occupies the resulting lead connector receiving bore or receptacle, and the DF4/IS4 assembly is being positioned for insertion into a predefined bore in the injection molded header that includes the rest of the connector assembly.

As depicted at 420 of FIG. 4, and shown in more detail in FIG. 6, as part of the process of assembling the header connector assembly 22, the DF4/IS4 assembly 48 has been assembled on the core pin 50, the core pin occupies the resulting lead connector receiving bore or receptacle 30, and the DF4/IS4 assembly 48 is positioned for insertion into the respective predefined bore 62 in the injection molded header 40 to become part of the overall connector assembly 42 [block 520].

As shown in FIG. 6, the core pin 50 extends through the open centers 59 of the strain relief 54, four seal assemblies 56, and the three contact assemblies 58 such that the strain relief, four seal assemblies and three contact assemblies are stacked together with the strain relief on the extreme distal end of the core pin and the order of the other elements being seal assembly, contact assembly, seal assembly, contact assembly, seal assembly, contact assembly, and seal assembly, moving distal to proximal along the stacked components of the DF4/IS4 assembly 48.

So far in the process as discussed above and as can be understood from FIGS. 4-6, the header 40 is first injection molded about the DF4/IS4 tip block 64 [block 510], which is located at the interior end (i.e., extreme proximal end) of the predefined bore 62 in the injection molded header 40. As reflected at 430 of FIG. 4, the assembled DF4/IS4 assembly 48 is proximally inserted into the predefined bore 62 to become part of the connector assembly 42 such that the proximal free end of the core pin 50 leads into the bore 62 to be eventually fully received in a central opening of the tip block 64 when the DF4/IS4 assembly 48 is fully received in the bore 62 [block 530]. As indicated at 430 in FIG. 4, the ribbons 70 are welded to the conductors and the carriers 72 are removed [block 535], thereby completing the header connector assembly 22.

As shown at 440 of FIG. 4, the header connector assembly 22 is welded to the can or housing 24 [block 540]. Specifically, the ribbons 70 are welded to the feedthru of the can or housing 24. Per 450, the header connector assembly 22 is epoxy backfilled at the location indicated by Arrow A [block 550]. Finally, as shown at 460, septums 74 are installed to complete the IPG [block 560].

C. Keyed Interface of Strain Relief and Predefined Bore of Injection Molded Header.

As can be understood from FIGS. 3-6 and explained above, during the process of assembling the connector assembly 42 and the header connector assembly 22, the DF4/IS4 tip block 64 is not initially part of the DF4/IS4 assembly 48, but is instead part of the overmolded header 40. As illustrated in FIGS. 4 and 6, the DF4/IS4 tip block 64 is molded into the header 40 and awaits to receive of the proximal free end of the core pin 50 when the DF4/IS4 assembly 48, and its supporting core pin 50, are inserted as a whole into the predefined bore 62 in the injection molded header 40 to become part of the overall connector assembly 42.

Figure 9:
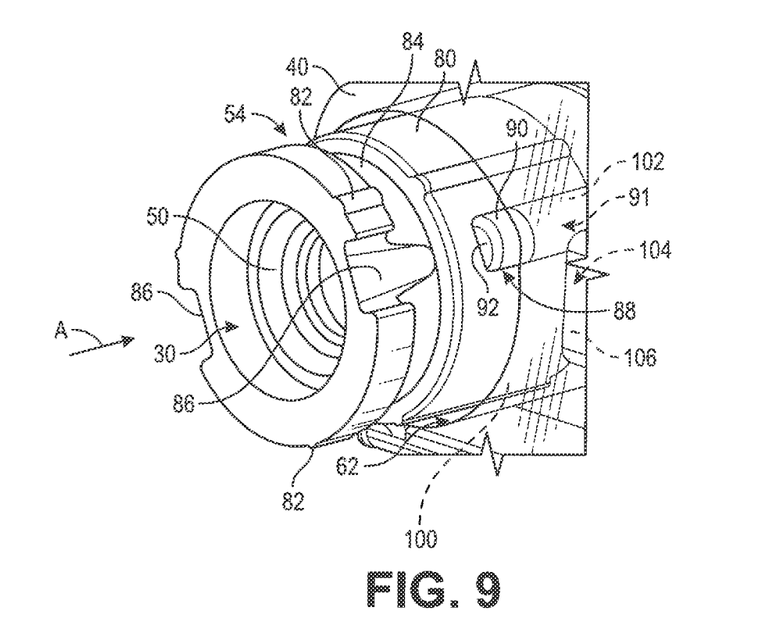
FIG. 9 is an enlarged isometric view of the DF4/IS4 assembly, and more specifically, the strain relief, being received in the predefined bore in the injection molded header.
Figure 10:
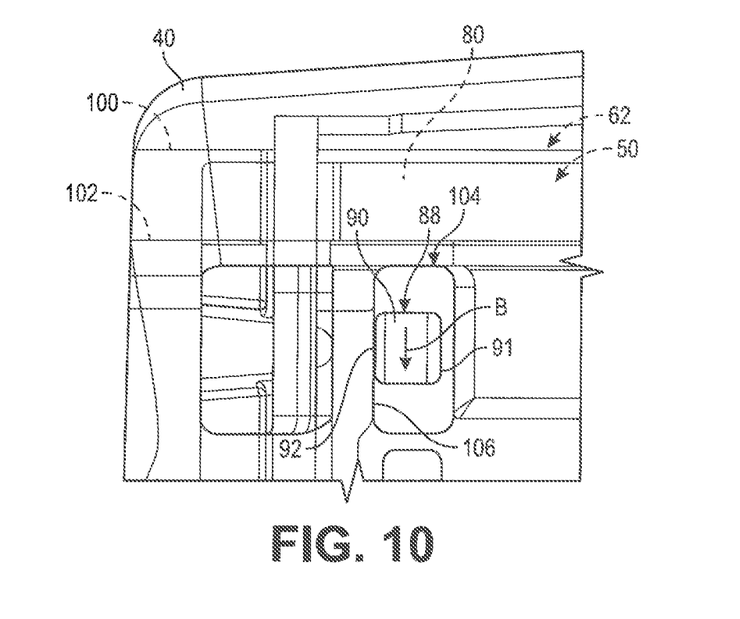
FIG. 10 is an enlarged side view of the DF4/IS4 assembly fully received in the predefined bore in the injection molded header, the key occupying the datum notch and the distal face of the key abutting the distal datum wall in planar contact.
Figure 11:
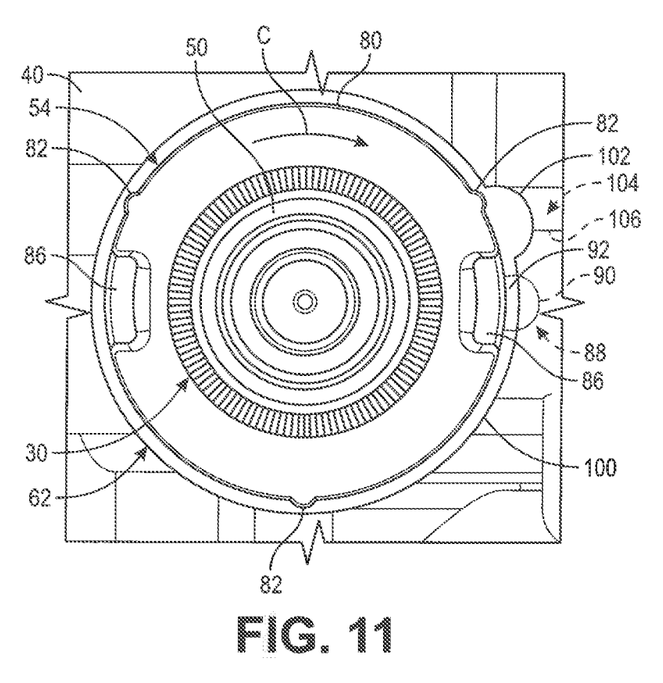
FIG. 11 is an enlarged distal end view of the DF4/IS4 assembly in the situation depicted in FIG. 10.

Without the DF4/IS4 tip block being part of the DF4/IS4 assembly 48, the stack of components 54, 56, 58 of the DF4/IS4 assembly 48 (see FIG. 3) can not be locked as a sub-assembly prior to installation into the predefined bore 62 in the injection molded header 40. Thus, the components 54, 56, 58 of the DF4/IS4 assembly 48 are placed onto the inner core pin 50 and immediately installed into the predefined bore 62 in the injection molded header 40, as reflected in FIGS. 3, 4 and 6. To avoid the need to fixture and locate the pre-molded header 40, the strain relief 54 and predefined bore 62 in the injection molded header 40 have been keyed to accept a locking feature, as discussed below with respect to FIGS. 7 and 8. This keyed interface between the strain relief 54 and the bore 62 allows the user to simply insert and rotate the strain relief 54 using tweezers or a spanner bit to "Twist and Lock" the DF4/IS4 assembly 48 into place within the bore 62, as shown in FIGS. 9-11 and discussed below.

Figure 7:
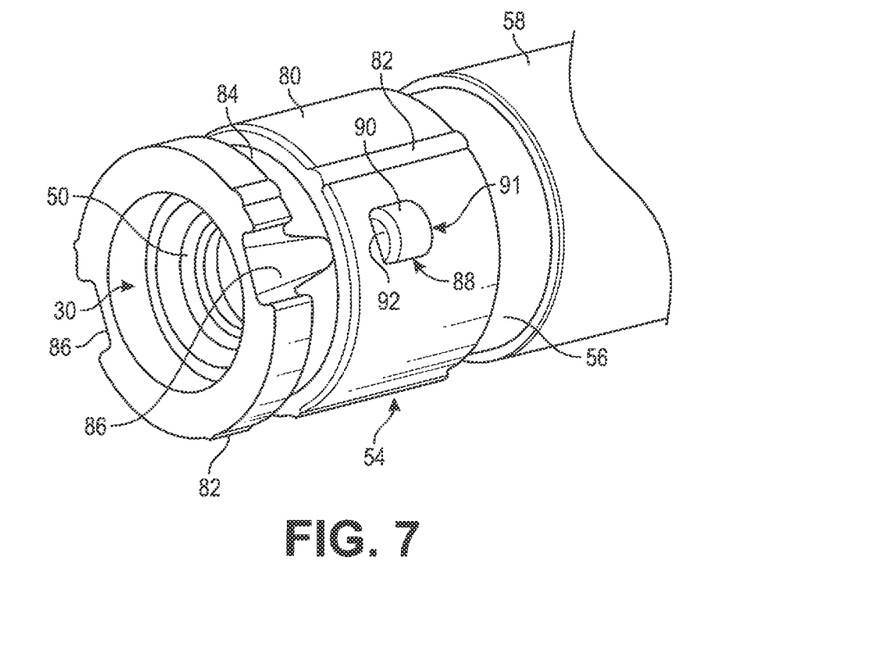
FIG. 7 is an enlarged isometric view of a distal end of the strain relief of the DF4/IS4 assembly of FIG. 6.

As indicated in FIG. 7, which is an enlarged isometric view of a distal end of the strain relief 54 of the DF4/IS4 assembly 48 of FIG. 6, the strain relief includes a cylindrical outer circumferential surface 80. Defined on or in the outer circumferential surface 80 of the strain relief may be a number of features, including, for example, a number of longitudinally extending radially protruding ribs 82 extending proximal-distal on the strain relief, a circumferentially extending and radially recessed groove 84 near the distal end of the strain relief, and a pair of opposed notches 86 extending proximally from the distal end of the strain relief and spaced 180 degrees from each other about the outer circumferential surface of the strain relief 50. These notches 86 taper as they proximally extend from the distal end of the strain relief and can be used as assembly tool engagement features to be engaged by a tool (e.g., tweezers, spanners, etc.) to cause the DF4/IS4 assembly 48 to rotate about the longitudinal axis of the core pin 50 when the DF4/IS4 assembly 48 and its supporting core pin 50 are being installed into the predefined bore 62 in the injection molded header 40, as reflected in FIGS. 3, 4 and 6.

As illustrated in FIG. 7, the key 88 radially projects from the outer circumferential surface 80 of the strain relief 54 and is located proximal of the groove 84. In one embodiment, the key 88 includes an arcuate lateral or side surface 90 that extends distal-proximal between a proximal face 91 and a distal face 92 that is opposite the proximal face, both faces being perpendicular to the side surface 90. As a result of such a configuration, the key 88 can be said to have a half-disc shape or semi-circular shape, as can be understood from FIG. 7. The faces 91, 92 are perpendicular to a longitudinal center axis of the DF4/IS4 assembly 48.

In one embodiment, arcuate lateral surface 90 has a radius of approximately 0.025". In other embodiments, the radius can be smaller or larger.

Figure 8:
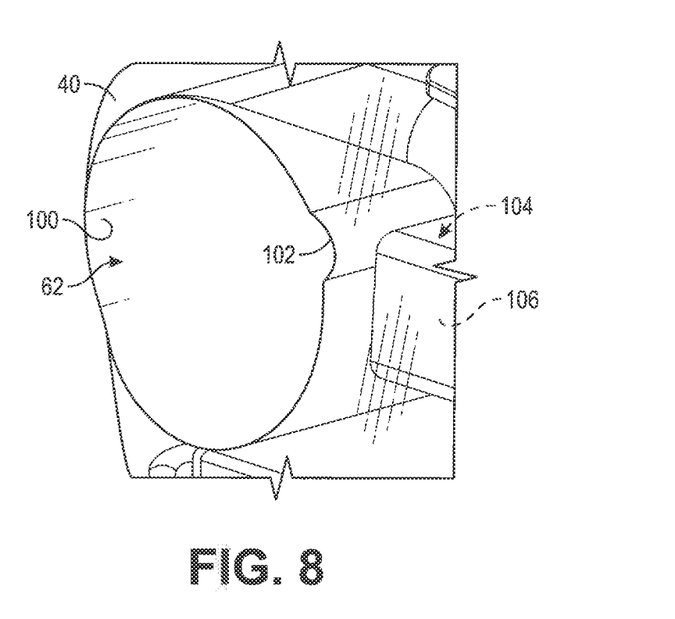
FIG. 8 is an enlarged isometric view of a distal end of the the predefined bore in the injection molded header of FIG. 6.

As depicted in FIG. 8, which is an enlarged isometric view of a distal end of the the predefined bore 62 in the injection molded header 40 of FIG. 6, the bore 62 includes a cylindrical inner circumferential surface 100. This inner circumferential surface 100 is of a complementary or corresponding shape and size relative to the outer circumferential surface 80 of the strain relief 54 of FIG. 7 such that the bore 62 can receive the DF4/IS4 assembly 48, and more specifically, the strain relief 54 in mating fashion, as can be understood from FIG. 4.

As illustrated in FIG. 8, the longitudinally extending groove 102 extends distal-proximal in the inner circumferential surface 100 from the distal opening of the bore 62. The groove 102 is of a shape and size that is complementary and corresponding to the shape of the key 88 such that the groove 102 can receive the key 88 as the strain relief 54 proximally moves within the bore 62 as the DF4/IS4 assembly 48 is inserted into the bore 62, as can be understood from FIG. 4.

In one embodiment, the groove 102 has a diameter of approximately 0.053". In other embodiments, the diameter can be smaller or larger.

As reflected in FIG. 8, a datum notch 104 extends perpendicularly from the groove 102 and the inner circumferential surface 100 of the bore 62. The datum notch 104 includes a distal datum wall 106 that is perpendicular to a longitudinal center axis of the bore 62 and the inner circumferential surface 100 of the bore 62.

In one embodiment, the datum notch has a distal-proximal width between its distal datum wall 106 and its proximal datum wall of approximately 0.055". In other embodiments, the width can be smaller or larger.

In one embodiment, the key and datum notch may be designed to be injection moldable without undercut.

As can be understood from FIG. 4 and, more particularly, FIG. 9, which is an enlarged isometric view of the DF4/IS4 assembly 48, and more specifically, the strain relief 50, being received in the predefined bore 62 in the injection molded header 40, the key 88 is aligned with, and slid into, the groove 102 to allow the strain relief, and by extension, the DF4/IS4 assembly, to fully enter the bore 62. Arrow A indicates the proximal displacement of the DF4/IS4 assembly 48 relative to the injection molded header 40 as the key 88 is aligned with and enters the groove 102 while the DF4/IS4 assembly 48 is received in the bore 62.

FIGS. 10 and 11 are, respectively, an enlarged side view and an enlarged distal end view of the DF4/IS4 assembly 48 fully received in the predefined bore 62 in the injection molded header 40, the key 88 occupying the datum notch 104 and the distal face 92 of the key 88 abutting the distal datum wall 106 in planar contact. As can be understood from FIGS. 9-11, once the DF4/IS4 assembly 48 has been fully received in the bore 62 and the key 88 has become aligned with the datum notch 104, the DF4/IS4 assembly can be rotated clockwise to cause the key 88 to move from the groove 102 and into the datum notch 104. Arrows B and C in FIGS. 10 and 11, respectively, indicate the clockwise rotation of the DF4/IS4 assembly 48 within the bore 62 and relative to the injection molded header 40, thereby causing the key 88 to leave the confines of the groove 102 and enter the confines of the datum notch 104. The distal face 92 of the key 88 abuts against the distal datum wall 106 in planar contact, thereby locking the DFT/IS4 assembly 48 fully inserted in the predefined bore 62 and preventing the DF4/IS4 assembly 48 from distally withdrawing from the bore 62. The manufacturing process then continues as outlined above in FIG. 4 at 430, 440, 450 and 460 and also FIG. 5 at 530, 535, 540, 550 and 560.

The embodiments of the push and twist keyed locking datum arrangement described above are provided in the context of the key being located on the DF4/IS4 assembly and, more specifically, on the exterior of the strain relief, and the datum being a complementary recess in the header and, more specifically, a complementary recess radially extending from the bore of the header. In other words, the locking datum arrangement described above includes a male portion of the DF4/IS4 arrangement interfacing in a male/female locking arrangement with a female portion of the header.

In other embodiments, the push and twist keyed locking datum arrangement can be reversed such the key is located on the header and the datum is located on the DF4/IS4 assembly and, more specifically, on the strain relief. In other words, the locking datum arrangement may be configured to include a female portion of the DF4/IS4 arrangement interfacing in a male/female locking arrangement with a male portion of the header.

In summary, on account of the keyed locking datum arrangement between the strain relief of the DF4/IS4 assembly and the bore of the injection molded header, the DF4/IS4 assembly can be simply inserted and twisted or rotated using tweezers or a spanner bit. Thus, the twist and lock interface between the strain relief and the bore of the injection molded header is advantageous because the keyed locking datum arrangement allows the DF4/IS4 assembly to be aligned, inserted, rotated, compressed, and locked together within the bore without the use of additional tooling. The keyed locking datum arrangement provides the axial compression required within the DF4/IS4 assembly to prevent epoxy from leaking into the components and spaces of the DF4/IS4 assembly when the DF4/IS4 assembly is being encapsulated in epoxy during the backfill process, and this benefit is provided without the use of any additional tooling or set screws. Additionally, there is no risk of damaging the pre-molded headers in tooling, no set screw is required to lock, and the keyed locking datum arrangement removes the variability in axial compression caused by manufacturing via an arbor press.

The foregoing merely illustrates the principles of the invention. Various modifications and alterations to the described embodiments will be apparent to those skilled in the art in view of the teachings herein. It will thus be appreciated that those skilled in the art will be able to devise numerous systems, arrangements and methods which, although not explicitly shown or described herein, embody the principles of the invention and are thus within the spirit and scope of the present invention. From the above description and drawings, it will be understood by those of ordinary skill in the art that the particular embodiments shown and described are for purposes of illustrations only and are not intended to limit the scope of the present invention. References to details of particular embodiments are not intended to limit the scope of the invention.

What is claimed is:

1. A method of manufacturing an implantable electronic device, the method comprising:
    inserting a DF4/IS4 assembly into a bore of a header, the DF4/IS4 assembly defining a receptacle configured to receive a lead connector end of an implantable lead; and
    rotating the DF4/IS4 assembly within the bore to engage a locking datum arrangement that exists between the DF4/IS4 assembly and the header, the locking datum arrangement preventing the DF4/IS4 assembly from being withdrawn from the bore.

2. The method of claim 1, wherein the DF4/IS4 assembly is supported on a core pin when the DF4/IS4 assembly is inserted into the bore.

3. The method of claim 2, wherein the header includes a tip block embedded in the header, a free end of the core pin projects proximally from the DF4/IS4 assembly, and the free end is received in the tip block before the DF4/IS4 assembly is rotated to engage the locking datum arrangement.

4. The method of claim 1, wherein the bore includes a groove that extends proximally from a distal opening of the bore, the DF4/IS4 assembly includes a key radially extending from the DF4/IS4 assembly, and the key moves along the groove when the DF4/IS4 assembly is inserted into the bore.

5. The method of claim 4, wherein a datum notch extends from the bore into the header, and rotating the DF4/IS4 assembly causes the key to extend into the datum notch, thereby engaging the locking datum arrangement.

6. The method of claim 1, wherein engaging the locking datum arrangement compresses the DF4/IS4 assembly.

7. The method of claim 1, wherein the DF4/IS4 assembly and the header, when locked together via the locking datum arrangement, form at least part of a header connector assembly, the method further comprising welding the header connector assembly to a housing of the implantable electronic device.

8. The method of claim 7, further comprising epoxy backfilling the header connector assembly.

9. The method of claim 1, wherein the implantable electronic device is an implantable pulse generator.

10. A method of manufacturing an implantable electronic device, the method comprising:
   inserting a DF4/IS4 assembly into a bore of a header, the DF4/IS4 assembly defining a receptacle configured to receive a lead connector end of an implantable lead; and
   rotating the DF4/IS4 assembly within the bore to engage a locking datum arrangement that exists between the DF4/IS4 assembly and the header, the locking datum arrangement preventing the DF4/IS4 assembly from being withdrawn from the bore, wherein:
   the DF4/IS4 assembly includes a first portion of the locking datum arrangement,
   the header further defines a second portion of the locking datum arrangement disposed along the bore and forming an interface with the first portion of the locking datum arrangement, and
   the DF4/IS4 assembly is locked within the bore via the interface between the first portion of the locking datum arrangement and the second portion of the locking datum arrangement.

11. The method of claim 10, wherein the DF4/IS4 assembly is supported on a core pin when the DF4/IS4 assembly is inserted into the bore.

12. The method of claim 11, wherein the header includes a tip block embedded in the header, a free end of the core pin projects proximally from the DF4/IS4 assembly, and the free end is received in the tip block before the DF4/IS4 assembly is rotated to engage the locking datum arrangement.

13. The method of claim 10, wherein the bore includes a groove that extends proximally from a distal opening of the bore, the DF4/IS4 assembly includes a key radially extending from the DF4/IS4 assembly, and the key moves along the groove when the DF4/IS4 assembly is inserted into the bore.

14. The method of claim 13, wherein a datum notch extends from the bore into the header, and rotating the DF4/IS4 assembly causes the key to extend into the datum notch, thereby engaging the locking datum arrangement.

15. The method of claim 10, wherein engaging the locking datum arrangement compresses the DF4/IS4 assembly.

16. The method of claim 10, wherein the DF4/IS4 assembly and the header, when locked together via the locking datum arrangement, form at least part of a header connector assembly, the method further comprising welding the header connector assembly to a housing of the implantable electronic device.

17. The method of claim 16, further comprising epoxy backfilling the header connector assembly.

18. The method of claim 10, wherein the implantable electronic device is an implantable pulse generator.

19. A method of manufacturing an implantable electronic device, the method comprising:
   inserting a connector assembly into a bore of a header, the connector assembly defining a receptacle configured to receive a lead connector end of an implantable lead; and
   engaging a locking datum arrangement that exists between the connector assembly and the header, the locking datum arrangement preventing the connector assembly from being withdrawn from the bore,
   wherein:
   the connector assembly includes a first portion of the locking datum arrangement,
   the header further defines a second portion of the locking datum arrangement disposed along the bore and forming an interface with the first portion of the locking datum arrangement, and
   the connector assembly is locked within the bore via the interface between the first portion of the locking datum arrangement and the second portion of the locking datum arrangement.

20. The method of claim 19, wherein engaging the locking datum arrangement comprises rotating the connector assembly within the bore.

* * * * *